United States Patent [19]

Hruska

[11] Patent Number: 4,681,999

[45] Date of Patent: Jul. 21, 1987

[54] APPARATUS FOR WELDING DENTAL ELEMENTS

[76] Inventor: Arturo Hruska, Via G. Carducci 10, 00187 Rome, Italy

[21] Appl. No.: 711,100

[22] Filed: Mar. 13, 1985

[30] Foreign Application Priority Data

Jun. 20, 1984 [IT] Italy .............................. 48426 A/84
Aug. 28, 1984 [IT] Italy .............................. 48767 A/84

[51] Int. Cl.$^4$ ............................................ B23K 11/26
[52] U.S. Cl. ...................................... 219/111; 219/90; 219/113
[58] Field of Search ................ 219/90, 110, 113, 111, 219/108

[56] References Cited

U.S. PATENT DOCUMENTS

| | | | |
|---|---|---|---|
| 2,179,497 | 11/1939 | Davitow ................................ | 219/90 |
| 2,342,594 | 2/1944 | Mesch et al. .......................... | 219/90 |
| 2,464,054 | 3/1949 | Panik ..................................... | 219/90 |
| 2,689,899 | 9/1954 | Faulk et al. ............................ | 219/90 |
| 3,899,653 | 8/1975 | Spinnato ............................... | 219/113 |
| 4,458,132 | 7/1984 | Reynolds et al. ..................... | 219/113 |

FOREIGN PATENT DOCUMENTS 443437 2/1936 United Kingdom ................. 219/90

*Primary Examiner*—Clifford C. Shaw
*Attorney, Agent, or Firm*—John J. Byrne

[57] ABSTRACT

A precision electric welding device is used for welding dental crowns and bridges in the mouth, the dental elements to be welded being made up of dentally suitable metals, especially of titanium and titanium alloys. The device comprises, in combination, an electronic welding base unit supplied with direct current voltage source and provided with a storage device containing a plurality of welding sequences, each welding sequence defining the energy requirements for successive pulses in a particular welding operation. The base unit generates a series of controlled voltage potentials for each operation, and an interdental precision electric welding gun is responsive to said series of controlled voltage potentials for performing the welding operations. Features of the invention include provision, on the welding gun, of a threaded rotatable rod extending between electrically conductive arms of the gun and having an operator-rotatable disk for adjustment of the bias of a carriage spring, coaxially mounted on one of the arms, against a part received between electrodes located at tips of the arms of the gun.

18 Claims, 7 Drawing Figures

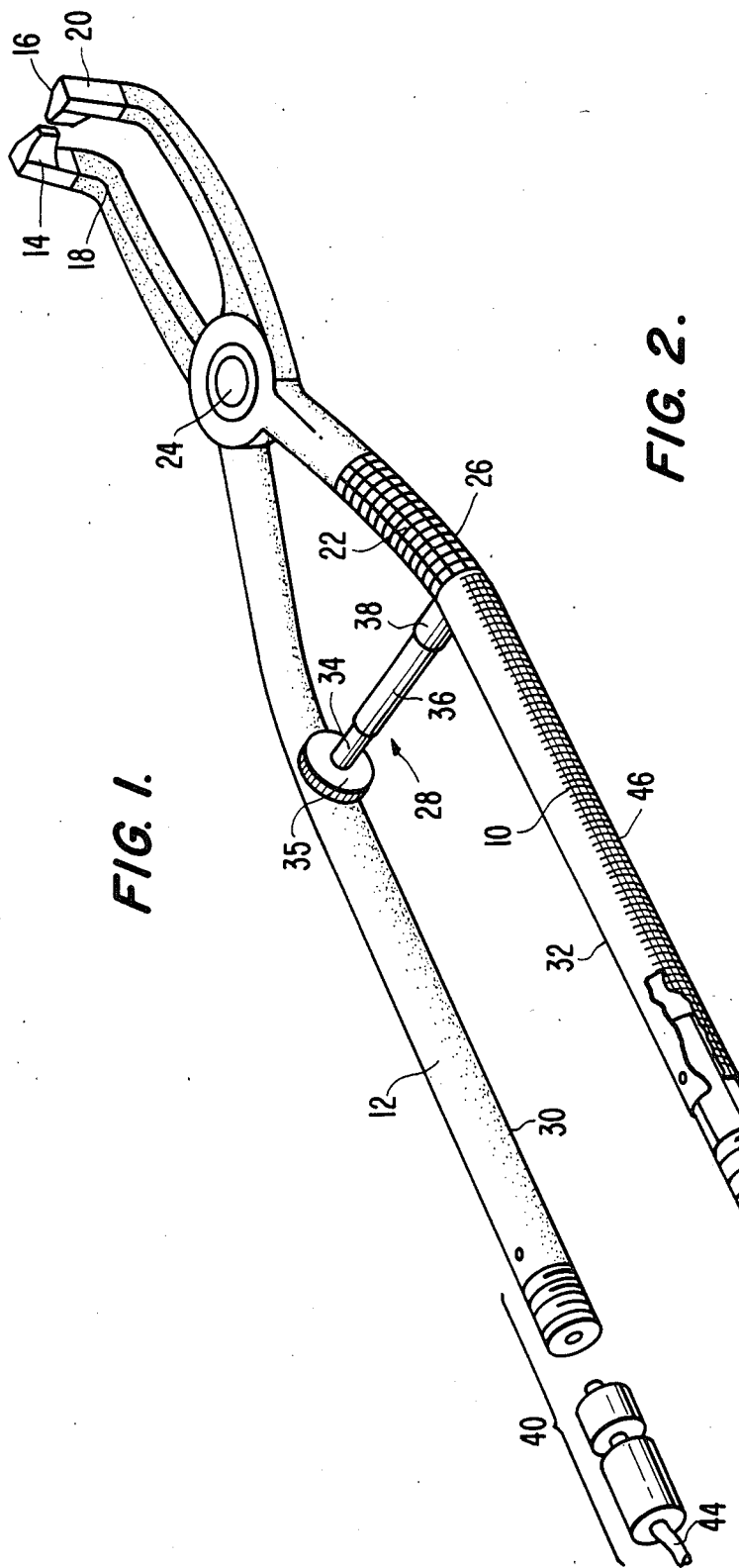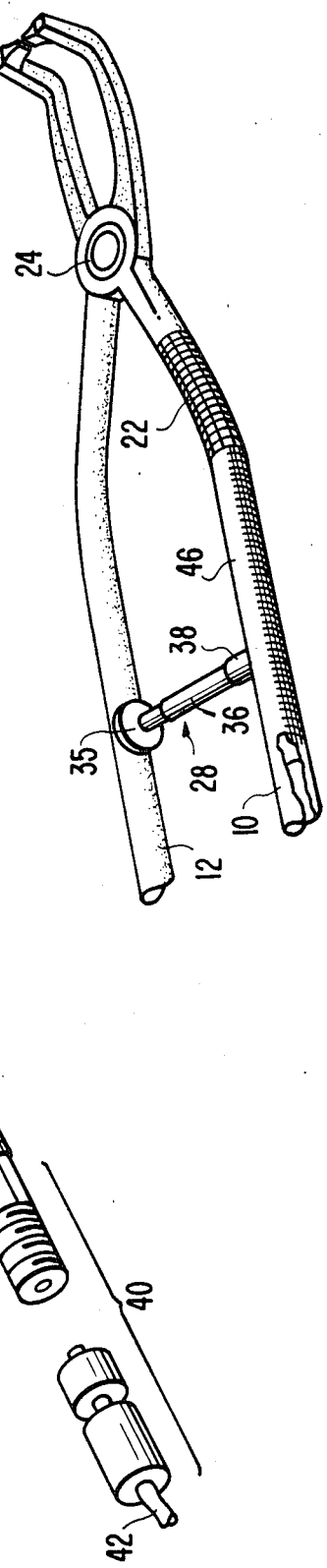

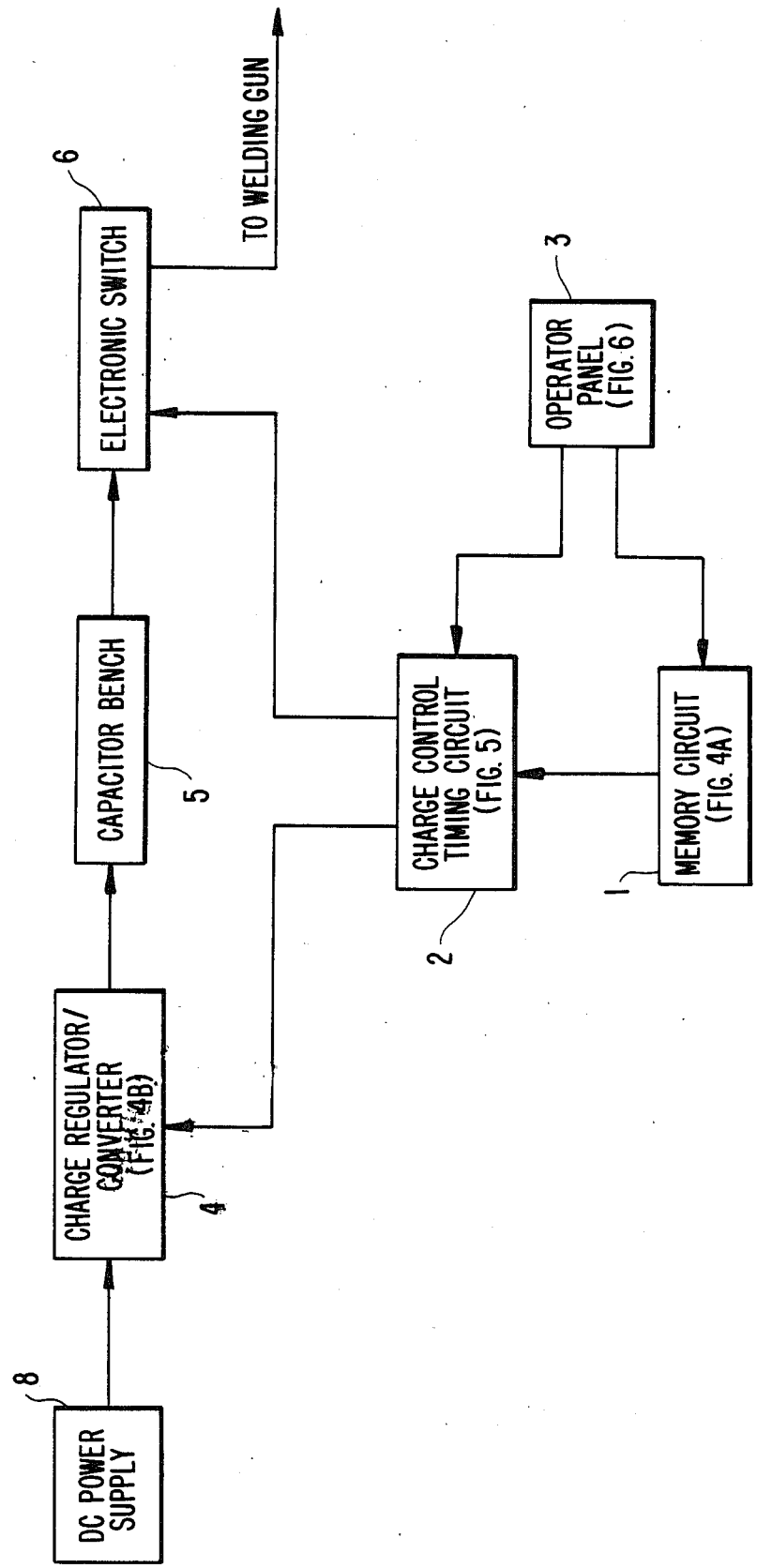

APPARATUS FOR WELDING DENTAL ELEMENTS

FIELD OF INVENTION

This invention relates to a precision electric welding device for welding dental elements including crowns and bridges in the mouth. The elements are made up of dentally suitable metals, especially of titanium and titanium alloys. The welding device comprises in combination with a precision electric welding gun and an electronic welding base unit connected thereto. The base unit is operative to provide a series of controlled voltage potentials to said welding gun, which potentials vary in magnitude in accordance with specific requirements of particular welding tasks. The welding gun makes actual contact with the dental elements to be welded, and applies voltage across said dental elements in accordance with the controlled voltage potentials supplied thereto by said base unit.

BACKGROUND OF THE INVENTION

The problems encountered by past makers of welding devices of the type similar to that of the instant invention are two-fold. The first is with regard to the precision welding gun, and the second is with regard to the capacitive discharge welding base unit.

Regarding the precision welding gun, an example of prior art welding guns is the electroholder gun described by the Italian Pat. No. 957,321 (Spinnato). In the Spinnato device, a helical spring is provided that forms a central fulcrum of its arms. The tips of said arms elastically engage and act so as to close the tips of the gun. The tips are opened only by exerting a force on the arms. The Spinnato structure does not permit the degree of sensitivity obtained by the device described herein.

Moreover, the Spinnato patent does not disclose the quick disconnect feature of this invention, either for its sterilization, or for its substitution with a gun bearing electrodes capable of satisfying different welding requirements. The gun according to the present invention satisfies this, as well as other requirements, advantageously.

Regarding the welding base unit, as is well known in the prior art, an example of prior art devices is an electric welding machine as that disclosed and illustrated in the Italian Pat. No. 957,322 (Spinnato). Spinnato's machine operates on alternating current, and it thus can be supplied only by network voltage, and is manually adapted each time for operation tailored to specific conditions of each welding task. Prior to operation, the setting or adaptation of the device requires a model experimentation to ensure proper operation of the device in real mode. Such preliminary checks are required because of possible changes in the network voltage supply and because of differences in the thickness of the materials to be welded as it is impossible to adjust the pressure of the welding gun employed with such welding devices in operation.

The welding base unit of the instant invention eliminates the aforementioned inconveniences and difficulties in the prior art. The instant unit is free of any problem given by voltage oscillations, as well as of risks to the operator caused by insulation losses relative to network voltage supply, because it is supplied by a direct current voltage source. Such a voltage source may originate from an accumulator or a storage battery, and is made possible by use of electronic components. Furthermore, the instant invention makes use of electronic memory storage in which respective energy requirements of successive voltage pulses in a welding operation are stored for execution upon operator selection and activation. The voltage potential and energy data specifically relate to welding operations as a function of changes in the characteristics of the materials for welding, and in the thickness and other characteristics relating to welding gun pre-loads. In this manner, exact welding operations tailored to various kinds of welding conditions may be reliably reproduced upon operator selection of predetermined voltage pulse sequences, without the need of model experimentation. It is also possible to display or print out the successive sequence information of the entire welding operation.

The device for welding dental elements in accordance with the present invention is suitable for carrying our welding operations in the mouth with any dentally compatible metal, especially with titanium or titanium alloys, for making bridges through the welding of preformed crowns provided with tabs, such as those disclosed in the Italian Patent Application No. 48426A/84 which are the object of said application, by using an interdental precision electric welding gun such as that disclosed in the Italian Patent Application No. 48425A/84 in the name of the same applicant as that of the present application.

OBJECTIVES OF INVENTION

It is a primary objective of the instant invention to provide a precision welding device for welding dental elements in the mouth which devices does not require specific adaptation via model experimentation prior to each welding task in order to ensure reliable reproduction of the desired effects.

It is an objective of the instant invention to provide a series of controlled voltage potentials from a capacitive discharge welding base unit to a precision electric welding gun by employing a direct current voltage source.

It is an objective of the instant invention to provide a welding device for welding dental elements in the mouth that makes use of pre-stored sequences of voltage pulse data tailored to specific welding conditions to generate a series of controlled voltage potentials in accordance therewith.

It is an objective of the instant invention to enable an operator to select a desired sequence of welding pulse requirements from one of many such pre-stored sequences.

It is an objective of the instant invention to facilitate the changing of voltage potential pulse requirements from one welding condition to another.

A principal objective of the present invention is to provide in said precision welding gun a means for adjusting the pressure on the parts to be welded by permitting the exertion of the desired constant pre-load pressure during welding by the electrodes as a result of the presence of a carriage spring and adjustment device.

It is a still further objective of the present invention to provide an electric welding gun having means to provide for the rapid engagement and disengagement of the cables from the welding machine power supply so that a gun can be readily and quickly replaced with another.

A further objective of the present invention is to provide prongs on which the electrodes are mounted at an angle with respect to the horizontal plane of the gun, the angle being advantageous for different welding requirements.

It is another objective of the present invention to supply a precision electric welding gun, particularly suitable for welding operations within the mouth, as well as in the orthopedic field or for other surgical applications, the gun including conductive levers crossing towards their tips at an electrically insulating fulcrum device.

Another objective of the invention is to provide replaceable electrodes at the tips of crossed levers with a high precision adjustment device between the arms of the levers together with a carriage spring on one of the levers downstream of the adjustment device, the unit being lined with a conductive flexible cord that restores the electric conductivity of the arm of said one of said levers and provides a rapid engagement/disengagement of the connector between the cables and the welding machine.

Another objective of the present invention is to provide a flexible cord conductor about said carriage spring.

A still further objective of this invention is to provide an electric welding gun that includes a high precision threaded rod on which a load adjusting disk is provided, and an insulating body on the opposite side of said disk to prevent the electric current from passing from one lever to another.

Other objects and advantages of the present invention will become apparent from the following detailed description of a preferred embodiment taken in conjunction with the accompanying drawings.

SUMMARY OF THE INVENTION

The subject welding apparatus includes an electronic welding base unit coupled to a precision welding gun for welding dental elements in the mouth.

The welding gun has structural and functional features that permit an optimal sensitivity in the grip of the user and the parts to be welded, and enable a capacity to preadjust the pressure exerted on said parts and to rapidly replace the gun with another similar gun provided with differently shaped electrodes.

The electronic welding base unit includes a direct current voltage source, a memory for pre-storing sequences of voltage potential requirements tailored to specific welding conditions, charging means for generating corresponding charge, capacitor means for maintaining said charge, and discharge means for applying a series of controlled voltage potentials of various magnitudes from said capacitor means to said precision welding gun.

According to one embodiment of the electric welding gun of this invention, the levers and the carriage spring are made of a Cu-Be alloy. The alloy is surface treated with a chromium plating to obtain a suitable equilibrium between the modulus of elasticity and mechanical strength so that the gun can be sterilized when disconnected.

According to another preferred embodiment of the invention, the gun carries its electrode-holder tips at a slope of any angle between 0° and 360° with respect to the horizontal plane of said gun depending on the particular welding requirements. The electric welding gun, when used in the dental field for welding operations within the mouth, normally carries its tips at an angle between 90° and 120° with respect to the horizontal plane of said gun.

BRIEF DESCRIPTION OF THE DRAWINGS

FIG. 1 is a perspective view of one embodiment of an electric welding gun according to the present invention.

FIG. 2 is a perspective view of another embodiment of the welding gun according to the present invention.

FIG. 3 shows an electrical pulse generator/discharger in accordance with the instant invention.

DETAILED DESCRIPTION

Figure 4A:
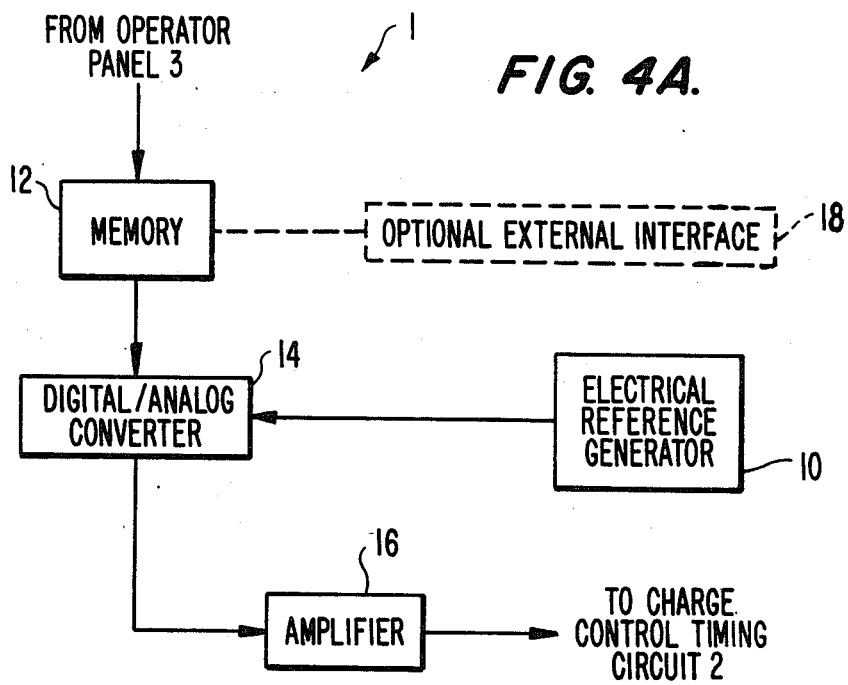
FIG. 4A shows the memory circuit of FIG. 3.

Referring to the drawings wherein like numbers indicate like parts, FIGS. 1 and 2 will be discussed first. The arms or levers of the electric welding gun according to this invention are indicated by the numerals 10 and 12. The levers 10 and 12 are constructed of a Cu-Be alloy surface-treated by a chromium plating so that sterilization of the gun is facilitated. The employment of such an alloy gives the welding gun a high electrical conductive as well as mechanical strength whereby an optimal compromise is reached between the modulus of elasticity and mechanical strength.

Elconite electrodes 14 and 16 are secured at the outer ends of tips 18 and 20 of the levers 10 and 12. The tips are bent to approximately 90° with respect to the plane of the welding gun as defined by movement of the levers 10 and 12. This configuration is particularly suitable for welding operations within the mouth.

Intermediate the length of lever 10, a carriage spring 22 is provided. The spring 22 is located where the levers begin to converge toward the fulcrum 24. The fulcrum 24 electrically insulates the lever 10 from the lever 12. A flexible copper lining 26 is provided about the carriage spring 22. The spring 22 is constructed of a Cu-Be alloy. The copper lining 26 restores the electrical conductivity of lever 10.

A pre-load adjusting device 28 extends between the handle sections 30 and 32 of levers 10 and 12, respectively. A threaded rotatable rod 34 having an operating disk 35 is received within a threaded member 36 so that a precision adjustment by the user can be made with the thumb of the hand that holds the welding gun. The threaded member 36 is secured to the handle 10 by a non-conductive stud 38. This prevents current from flowing between the levers.

By means of said precision adjusting device 28, it is possible to exert a selected constant pre-loading during the welding operation as a result of the force exerted by the carriage spring 22.

A rapid engagement and disengagement means 40 is located at the ends of the handle sections. The cables 42 and 44 of the welding unit control and the power supply (not shown) can be rapidly connected and disconnected to allow for the rapid replacement of a welding gun of a given shape with a gun of a different shape.

The levers at the fulcrum 24 are coated with plastic or other non-conductive material so as to prevent any short-circuiting of the current between levers 10 and 12. Additionally, all exterior elements of the gun, except the electrodes 14 and 16, are coated with a non-conductive coating indicated by the numeral 46.

In FIG. 2, there is shown a pre-load adjusting device 28 at a position between the straight sections of said levers 10 and 12.

In operation, the part or element to be welded is located between the electrodes 14 and 16. The disk or knob 35 is rotated until a desired pressure against the part is selected. Because of the carriage spring 26, this pressure has some resiliency and gives a "feel" to the gun user. After the welding has occurred, the pressure is released and a new weld can be performed. If the new weld requires a different size electrode or a different angle of tip with respect to the handles, the quick disconnect means can be used to quickly bring the new gun into action.

Referring now to the electrical pulse discharge unit in FIG. 3, a memory circuit 1 provides electrical analog signals corresponding to digital words stored in a memory therein. Each word represents the voltage pulse potential to be supplied to the welding gun, a series of such pulses constituting a welding operation. In a memory having 8-bit words, a total of 256 or $2^8$ variations of voltage potential may be conveniently accommodated. The stored data is first converted to analog via a digital/analog converter and then amplified to yield corresponding electrical analog signals as input to other circuits. In FIG. 4A, the memory circuit 1 is shown in detail, having an electrical reference generator 110, a memory unit 112, a digital/analog converter 114, and an amplifier 116. An optional external interface 118 for external data processing equipment (not shown) may be included, the data processing equipment serving to access, process, print, display or otherwise analyze the memory contents.

Figure 4B:
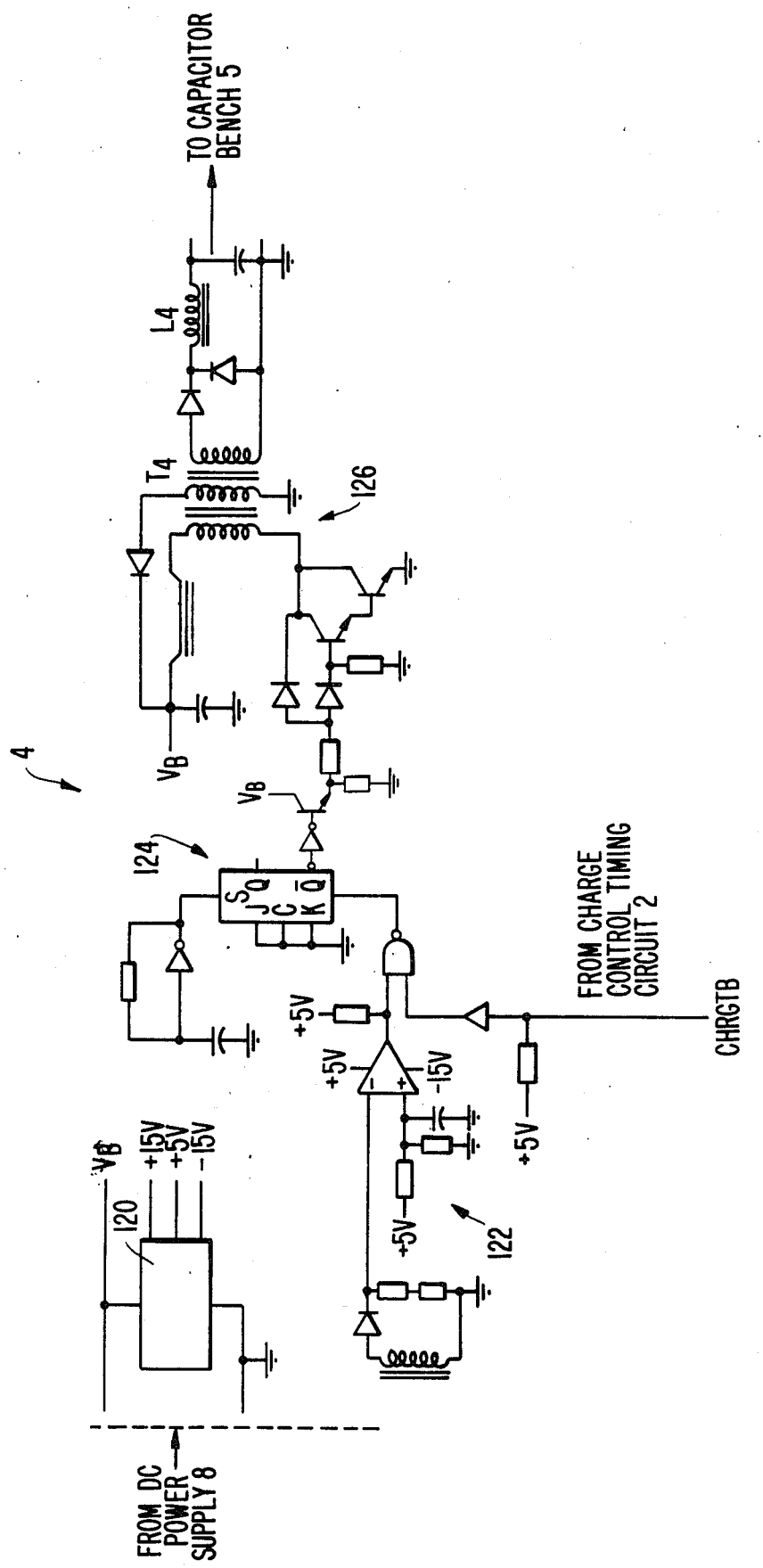
FIG. 4B shows the charge regulator/converter of FIG. 3.

FIG. 3 also shows a battery 8 representing a direct current voltage source or power supply, coupled to a charge regulator/converter 4 which generates charge corresponding to signals from the memory circuit 1 and from a charge control timing circuit 2. The charge effected via this unit corresponds to the value initially stored in the memory within the memory circuit 1. In FIG. 4B, the charge regulator/converter unit 4 is shown in detail, having a current limiter 122, a converter control circuit 124, a "forward" converter 126, and a power supply interface 120. The output from this charge regulator/converter 4 is coupled to a capacitor bench unit 5, in FIG. 3, comprising a bench of capacitive converters. The capacitor bench unit 5 is in turn coupled to an electronic switch unit 6 comprising an electronic switch pilot circuit and an electronic switch. The switch unit 6 is a driver circuit coupled to the welding gun for supplying a series of controlled voltage potentials thereto. It may comprise conventional electromechanical and analog integrated switches.

The charge derived via charge regulator/converter unit 4 is maintained in the capacitor bench unit 5 and later supplied to the welding gun via switch unit 6.

Figure 5:
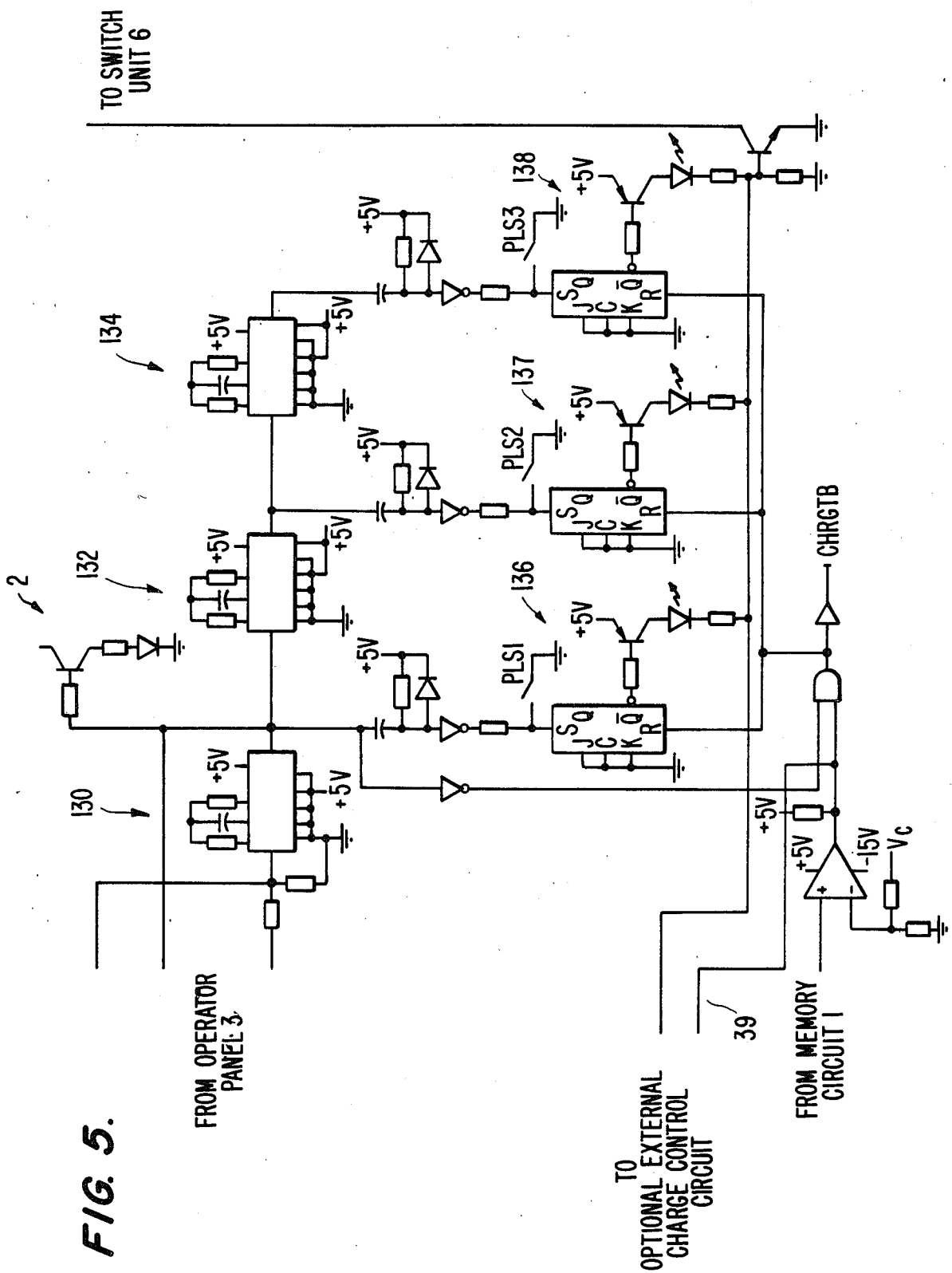
FIG. 5 shows the charge control timing circuitry of FIG. 3.

FIG. 3 further shows a charge control timing circuit 2 coupled to the memory circuit 1, the switch unit 6, and the charge regulator/converter unit 4, circuit 2 providing charge control timing signals thereto. It may include typically several timing devices and associated charge control circuitry. It represents an internal timebase circuit for effecting a series of controlled pulse generations in a welding operation. FIG. 5 shows this unit in detail, including an optional interface 139 to external charge control circuitry, the operation of which would displace the internal time-based circuits. In FIG. 5, internal timing circuits 130, 132, and 134 are respectively coupled to charge control circuits 136, 137, and 138. Interface 139 may connect to an external charge control circuit. The number of pulses in a welding sequence may be varied via interface 139 from an external controller (not shown). This external interface 139 is not necessary and the circuit of FIG. 5 supports a series of three voltage pulses of varying potential in a welding operation.

Figure 6:
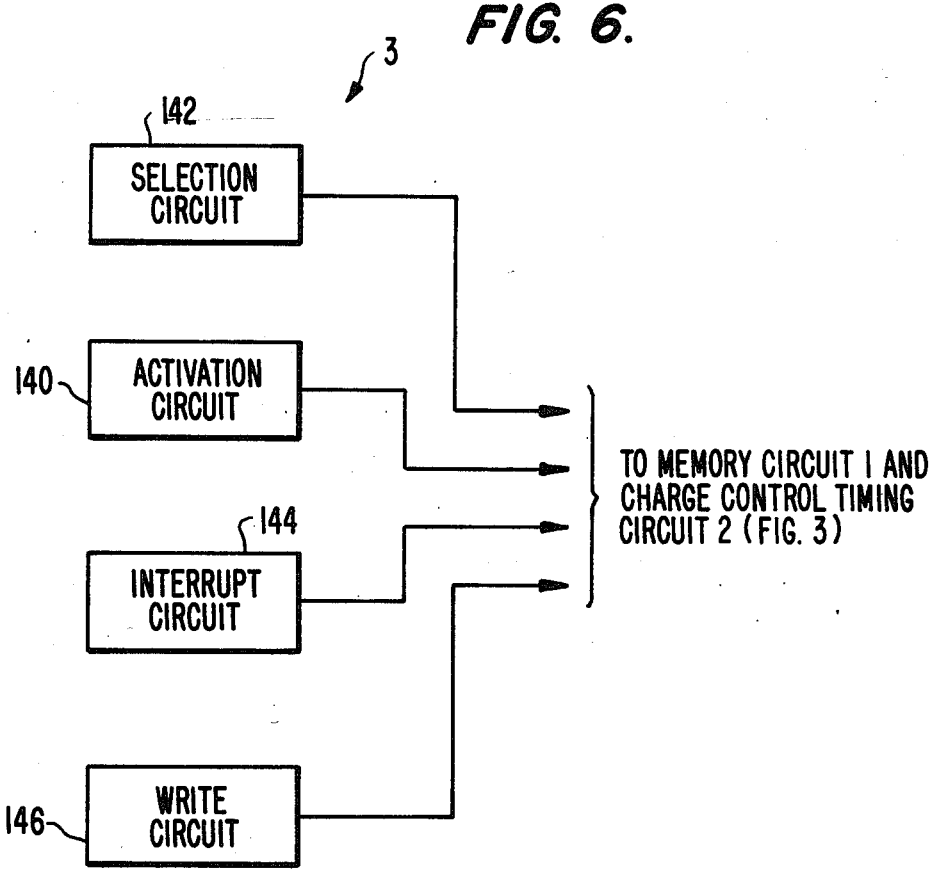
FIG. 6 shows the operator panel unit of FIG. 3.

FIG. 3 also shows an operator panel unit 3 coupled to the memory circuit 1 and to the charge control timing circuit 2. This operator panel unit 3 is shown in more detail in FIG. 6. It is coupled to both the memory circuit 1 and the charge control timing circuit 2. Unit 3 includes an activation circuit 140 for starting up the apparatus, a selection circuit 142 for selecting a welding sequence stored in the memory, an interrupt circuit 144 for halting operations, and a write circuit 146 (optional) for writing new sequences into memory, if the memory is writeable.

The above disclosure includes only some preferred embodiments of the instant invention. It is to be understood that changes and modifications within the confines of ordinary skill in the art may be introduced without departing from the spirit and scope of the inventive subject matter. In particular, it should be noted that the memory is not limited to an integrated digital memory device such as a ROM, PROM, or TAM; any memory may be suitable.

I claim:

1. A precision electric welding gun, comprising:
   first and second electrically conductive arms;
   pivoting means for pivotally interconnecting said first and second electrically conductive arms about a fulcrum axis, said first and second electrically conductive arms pivoting in a plane perpendicular to said fulcrum axis, said pivoting means dividing each of said electrically conductive arms into tips and handles;
   first and second electrodes mounted on said tips of said first and second electrically conductive arms, respectively, said first and second electrodes being movable toward and away from each other as said first and second electrically conductive arms are pivoted about said fulcrum axis;
   carriage spring means mounted coaxially along the length of said first electrically conductive arm and having a bias for exerting a spring-generated force along said first electrically conductive arm; and
   adjustment means for adjusting the bias of the carriage spring means against a workpiece received between said first and second electrodes;
   said adjustment means comprising a rod extending from said second electrically conductive arm to a point, on said first electrically conductive arm, adjacent to said carriage spring means, said carriage spring means being disposed between said point and said pivoting means.

2. The welding gun of claim 1, wherein one end of said rod comprises an operating disk which is rotatable about a lengthwise axis of said rod, said rod being threaded so that, when said operating disk is rotated, said rod is rotated and adjusts the separation between said first and second electrically conductive arms and the bias of the carriage spring means.

3. The welding gun of claim 2, wherein said operating disk is disposed adjacent to said second electrically conductive arm, said adjustment means further comprising a non-conductive stud disposed adjacent to said first electrically conductive arm for securing said rod thereto.

4. The welding gun of claim 1, wherein at least one of said first electrically conductive arm, said second electrically conductive arm and said carriage spring means are made of a Cu-Be alloy coated by chromium plating.

5. The welding gun of claim 4, wherein said carriage spring means is made of said Cu-Be alloy coated by chromium plating, and said gun further comprises a flexible copper lining formed over said carriage spring means.

6. The welding gun of claim 1, further comprising a flexible copper lining formed over said carriage spring means.

7. The welding gun of claim 1, wherein said tips of said first and second electrically conductive arms are disposed at a angle with respect to the plane in which said first and second electrically conductive arms pivot.

8. The welding gun of claim 1, wherein said first and second electrodes are made of elconite.

9. The welding gun of claim 1, wherein said pivoting means comprises an electrically insulating fulcrum mechanically interconnecting and electrically insulating said first and second electrically conductive arms with respect to each other.

10. An apparatus for performing a welding operation on dental crowns or bridges, said apparatus comprising:
   memory means for storing welding sequence data pertaining to a plurality of selectable welding sequences, each of said welding sequences comprising a plurality of pulses, said welding sequence data comprising voltage potential data for each of said plurality of pulses;
   operator control means for selecting at least one of said welding sequences for implementation during a desired welding operation, said operator control means generating corresponding control signals;
   charge control timing means responsive to said control signals from said operator control means for generating charge control timing signals;
   power supply means responsive to said charge control timing signals for generating a plurality of electrical pulses in accordance with said welding sequence data from said memory means corresponding to said at least one welding sequence selected by said operator control means; and
   welding gun means responsive to said plurality of electrical pulses for performing said welding operation.

11. The apparatus of claim 10, wherein said power supply means comprises a direct current power supply, a charge regulator/converter coupled to said direct current power supply and responsive to said welding sequence data from said memory means corresponding to said at least one welding sequence selected by said operator control means for providing an electrical charge for each said electrical pulse in the desired welding operation, capacitor circuitry connected to said charge regulator/converter for maintaining each said electrical charge provided by said charge regulator/converter at a given charge level, and an electrical switch responsive to the welding sequence data from said memory means corresponding to said at least one welding sequence selected by said operator control means for applying each said electrical charge to said welding gun means for a given period of time.

12. The apparatus of claim 10, wherein said operator selection means comprises an operator panel including a first switch for activating said charge control timing means and a second switch for interrupting said charge control timing means.

13. The apparatus of claim 12, wherein said memory means comprises a digital memory for storing the welding sequence data in digital form, a digital-to-analog converter connected to said digital memory for converting welding sequence data read from said digital memory to analog form so as to provide corresponding analog welding signals, and an amplifier for receiving and amplifying said analog welding signals prior to provision to said charge control timing means.

14. The apparatus of claim 10, wherein said memory means comprises a digital memory for storing the welding sequence data in digital form, a digital-to-analog converter connected to said digital memory for converting welding sequence data read from said digital memory to analog form so as to provide corresponding analog welding signals, and an amplifier for receiving and amplifying said analog welding signals prior to provision to said charge control timing means.

15. The apparatus of claim 14, wherein said memory means further comprises an external interface for communication with an external computer, said external interface acting to transfer welding sequence data between said memory means and said external computer.

16. The apparatus of claim 10, wherein said charge control timing means comprises an external interface for communication with an external computer, said external interface acting to transfer welding sequence data between said external computer and said charge control timing means.

17. The apparatus of claim 10, wherein said memory means comprises a read/write memory, said operation control means comprising operation-actuable controls for writing welding sequence information into said memory means.

18. The apparatus of claim 10, wherein each said electrical pulse in said desired welding operation is represented by a digital word in said memory means designating a corresponding voltage potential for said each said electrical pulse.

* * * * *